US006436259B1

(12) United States Patent
Russell

(10) Patent No.: US 6,436,259 B1
(45) Date of Patent: Aug. 20, 2002

(54) MERCURY SELECTIVE ELECTRODE

(75) Inventor: Dale D. Russell, Boise, ID (US)

(73) Assignee: Boise State University, Boise, ID (US)

( * ) Notice: Subject to any disclaimer, the term of this patent is extended or adjusted under 35 U.S.C. 154(b) by 0 days.

(21) Appl. No.: 09/144,574

(22) Filed: Aug. 31, 1998

(51) Int. Cl.[7] ............................................. G01N 27/26
(52) U.S. Cl. .................. 204/418; 204/416; 204/290 R; 422/82.03
(58) Field of Search ................................ 204/418, 416, 204/290; 436/81; 422/82.03

(56) References Cited

U.S. PATENT DOCUMENTS

| | | | | |
|---|---|---|---|---|
| 4,156,683 A | * | 5/1979 | Lehn | |
| 4,992,559 A | * | 2/1991 | Kathirgamanathan | |
| 5,519,147 A | * | 5/1996 | Swager et al. | |
| 6,060,327 A | * | 5/2000 | Keen | 436/518 |

OTHER PUBLICATIONS

Riyazuddin and Hussainy, "A Simply Mercury Ion Selective", 1986. *Educ. Chem.*, 23:146–147.
Brzozka and Petraszkiewicz, "Mercury Ion–Selective Polymeric Membrane Electrodes Based on Substituted Diaza Crown Ethers", 1991, *Electroanalysis* 3:855–858.
Shatkin, Brown and Licht, "Composite Graphite Ion Selective Electrode Array Potentionetry for the Dectection of Mercury and Other Relevant Ions in Aquatic Systems". *Anal. Chem.* 67:1147–1151.
Izatt, et al., "Thermodynamic and Kinetic Data for Cation–Macrocycle Interaction", 1985, *Chem. Rev.*, 85:271–339.
Bibliography (2 pages).

* cited by examiner

*Primary Examiner*—T. Tung
*Assistant Examiner*—Alex Noguerola
(74) *Attorney, Agent, or Firm*—Ken J. Pedersen; Barbara S. Pedersen

(57) ABSTRACT

The present invention is an apparatus for laboratory and field use in detecting and measuring $Hg^+$ and $Hg^{2+}$ in sample. A selective mercury binding agent, such as a chelating agent or clathrating agent, is covalently bound in a copolymer and deposited as an electrode layer. To prepare the preferred apparatus of the invention, thiophene, or other, similar monomer, is derivatized by covalent attachment thereto of Kryptofix-21™ (1,4,10-trioxa-7,13-diazacyclopentadecane) in the 3-position. The thiophene monomer and Kryptofix-21™ are co-polymerized and electrodeposited by known techniques onto a conductive substrate, such as platinum or glassy carbon, to obtain a multi-layer polymer coating of desired thickness. The resulting coated electrode has selective coordination sites for mercury of the order of $K_f=10^{16}$, compared to $K_f=10^3$ for cadmium, $K_f=10^5$ for lead and $K_f=10^5$ for silver. Therefore, the resulting probe is very selective for mercury, compared to cadmium, lead and silver.

10 Claims, 5 Drawing Sheets

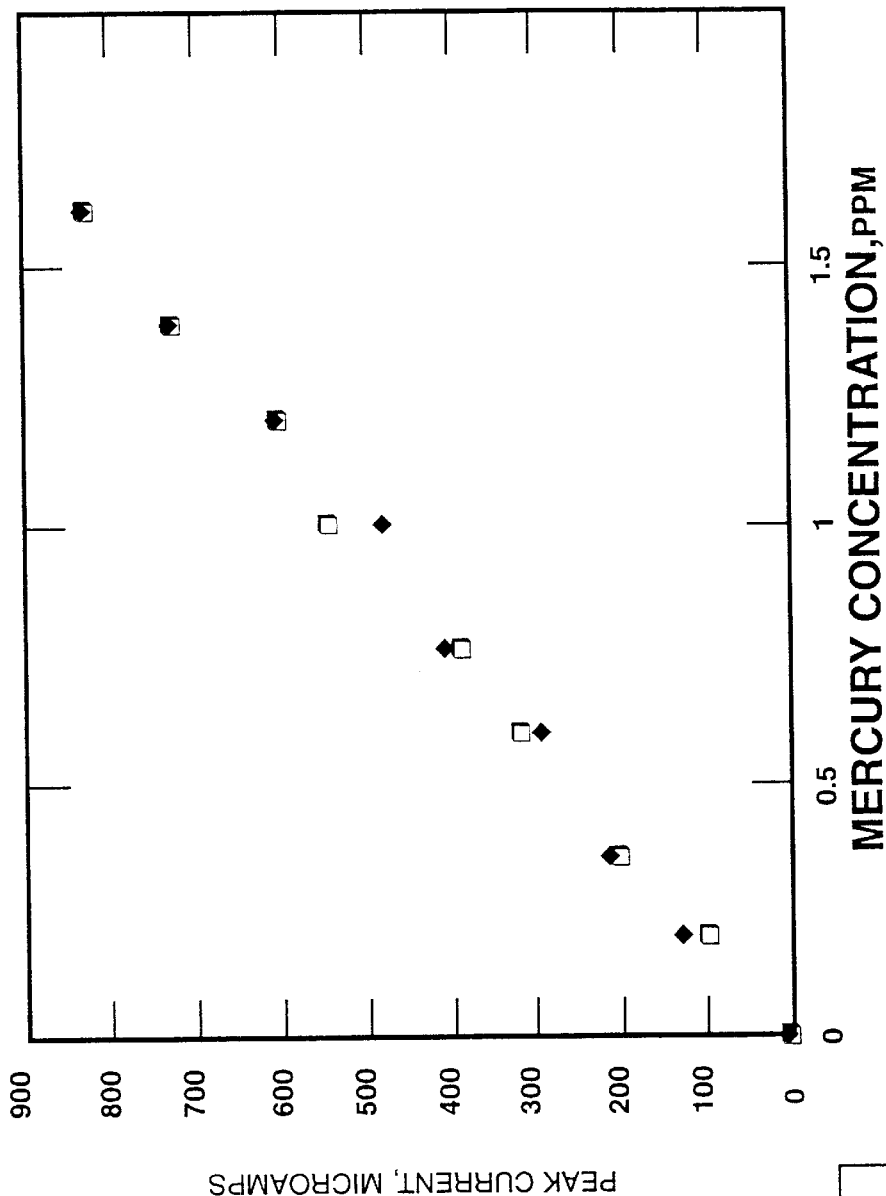

MERCURY SELECTIVE ELECTRODE

BACKGROUND OF THE INVENTION

1. Field of the Invention.

This invention relates generally to an apparatus and method for detecting and measuring $Hg^+$ and $Hg^{2+}$ in solution phase samples. More particularly, this invention relates to use of a selective electrical probe for $Hg^+$ and $Hg^{2+}$ containing a chelating or clathrating agent for mercury covalently bonded within an organic polymer matrix.

2. Related Art.

There is considerable interest in rugged, portable, hand-held, battery-powered sensors that yield results comparable to laboratory-based instruments. Mercury is of particular interest due to its toxicity, volatility, and the ease with which it is converted to forms that enter the environment and, ultimately, the food chain. Mercury in soil and water is taken up by plants and by animals that feed on the plants. In order to rapidly assess mercury contamination in the field, a rugged analytical device capable of detecting mercury at the ppb to sub-ppm level has long been sought.

Several potentiometric mercury electrodes have been demonstrated having detection limits as low as 2 ppm. Because environmental mercury contamination is usually in the ppb range, these potentiometric probes have not proven useful for field analysis. Most of these probes rely on random casts of a chelating agent to achieve mechanical entrapment of the chelating binding site in a liquid membrane. Loss of the chelating agent from the membrane by leaching over time results in fairly short working lifetimes, on the order of a few weeks.

An alternative approach for mercury measurement is based on substitution of $Hg^{2+}$ for $Ag^+$ in a halide crystal deposited on a graphite substrate. Detection limits for these substitution-type electrodes have been reported in the 2 ppb range, after a preconcentration step, which still makes them less useful for analysis in the field. Furthermore, this type of probe experiences significant interference from other ions such as cadmium (II), lead (II) and silver (I), which ions can also substitute to some extent into the crystal lattice, giving a false positive signal for mercury. These interferences reduce the selectivity and, ultimately, the utility of this measurement device.

Much work has been done in the general area of chelation of metals for electrochemical analysis. One of the more successful examples of this type of analytical device is the potassium ion selective electrode (ISE). This probe is based on incorporation of an 18-crown-6 ether macrocycle (e.g., Valinomycin™) into a polymeric membrane. The crown ether exhibits selective coordination for potassium even in the presence of sodium. The calcium ISE relies on a coordination interaction between calcium ions in the test solution and organophosphates suspended in a liquid ion exchange membrane coated onto a potentiometric probe. As the calcium is bound or released from the membrane, the surface potential changes in a fashion related to the natural logarithm of the calcium concentration.

Still, there is a need for a simple, reproducible and inexpensive probe for $Hg^+$ and $Hg^{2+}$. Also, there is a need for such a probe with a detection limit less than or equal to about 2 ppb with a long working lifetime, on the order of more than one year. Also, there is a need for such a probe with an amperometric response which is linear with mercury concentration over several orders of magnitude, and which is not significantly affected by dissolved oxygen, or by cadmium, lead or silver. The present invention addresses and satisfies these needs.

SUMMARY OF THE INVENTION

The present invention is an apparatus and method for detecting and measuring $Hg^+$ and $Hg^{2+}$ in samples. The invention comprises a copolymer of semi-conductive organic material including derivatized and underivatized monomers. The derivatizing functional group is a chelating and/or clathrating agent, chosen based on the agent's selectivity for coordination with the analyte metal, mercury. Preferably, the invented copolymer is deposited on a conductive substrate in order to construct a long-lived, economic instrument probe with a detection limit of less than about 2 ppb mercury in a fluid sample.

The preferred derivatizing functional group is 1,4,10-trioxa-7,13-diazacyclopentadecane, commercially available as Kryptofix-21™. This crown either has a high formation constant for complexations with mercury and is capable of stabilizing both members of the $Hg^+/Hg^{2+}$ couple.

To prepare the preferred apparatus of the invention, thiophene, or other, similar monomer, is derivatized by covalent attachment thereto of Kryptofix-21™ (1,4,10-trioxa-7,13-diazacyclopentadecane) in a position that will not be chain terminating during polymerization. The thiophene monomer and Kryptofix-21™ are co-polymerized and electrodeposited by known techniques onto a conductive substrate, such as platinum or glassy carbon, to obtain a multi-layer polymer coating of desired thickness. The resulting coated electrode has selective coordination sites for mercury having formation constants of the order $K_f=10^{16}$, compared to approximately $K_f=10^3$ for cadmium, $K_f=10^5$ for lead and $K_f=10^5$ for silver. Therefore, the resulting probe has the benefit of being very selective for mercury, compared to cadmium, lead and silver, and having a long working life due to the covalently bonding of the chelating agent in the probe surface.

BRIEF DESCRIPTION OF THE DRAWINGS

FIGS. 3, 4 and 5 are plots of experimental data from the worked Examples described below.

DESCRIPTION OF THE PREFERRED EMBODIMENTS

Figure 1A:
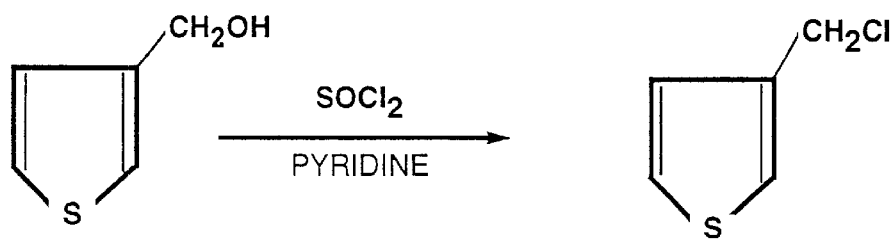
FIGS. 1A–1C are a schematic representation of steps for preparation of one embodiment of the electrode of the present invention.
Figure 1B:
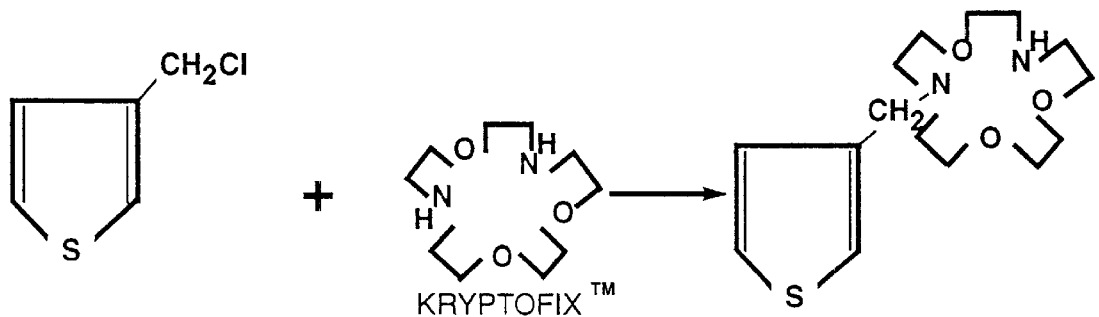
Figure 1C:
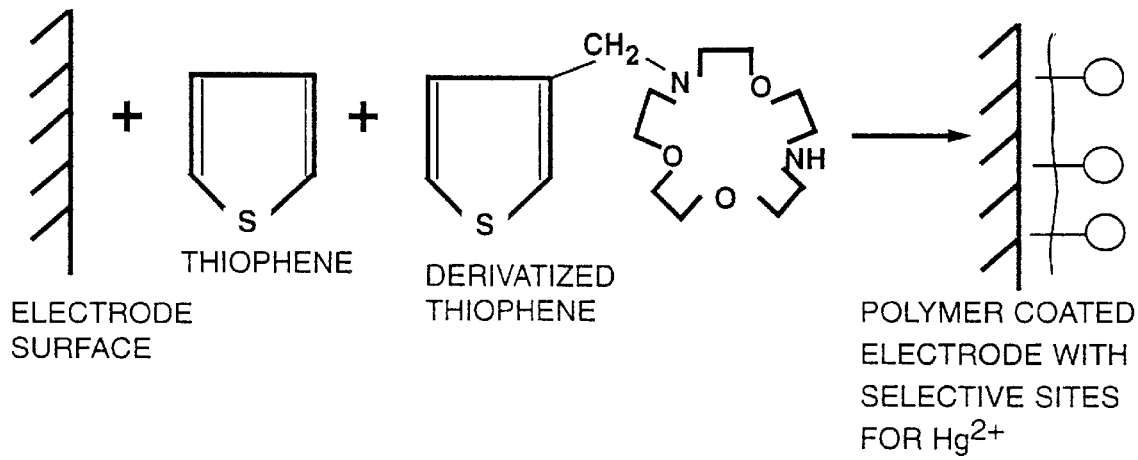
Figure 2:
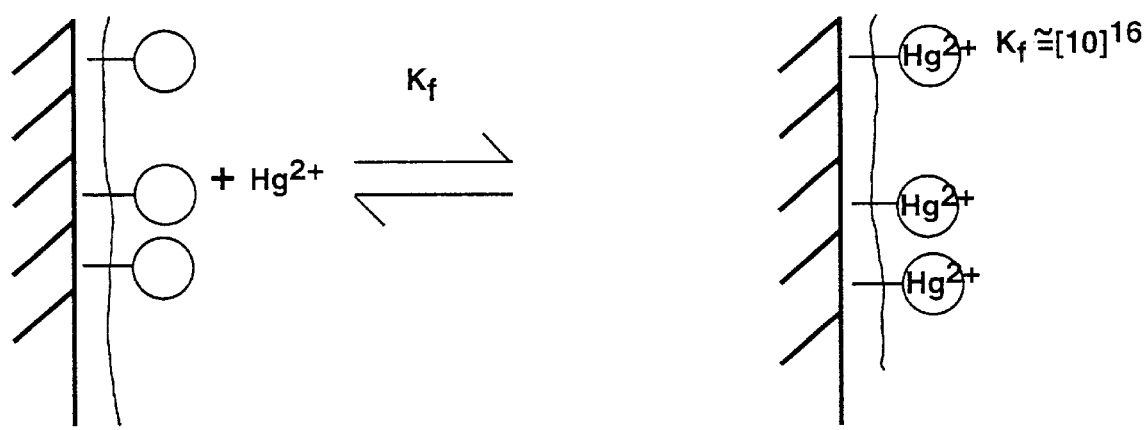
FIG. 2 is a schematic representation of the equilibrium chemistry of an embodiment of the electrode of the present invention in a solution containing mercury ion.
Figure 3:
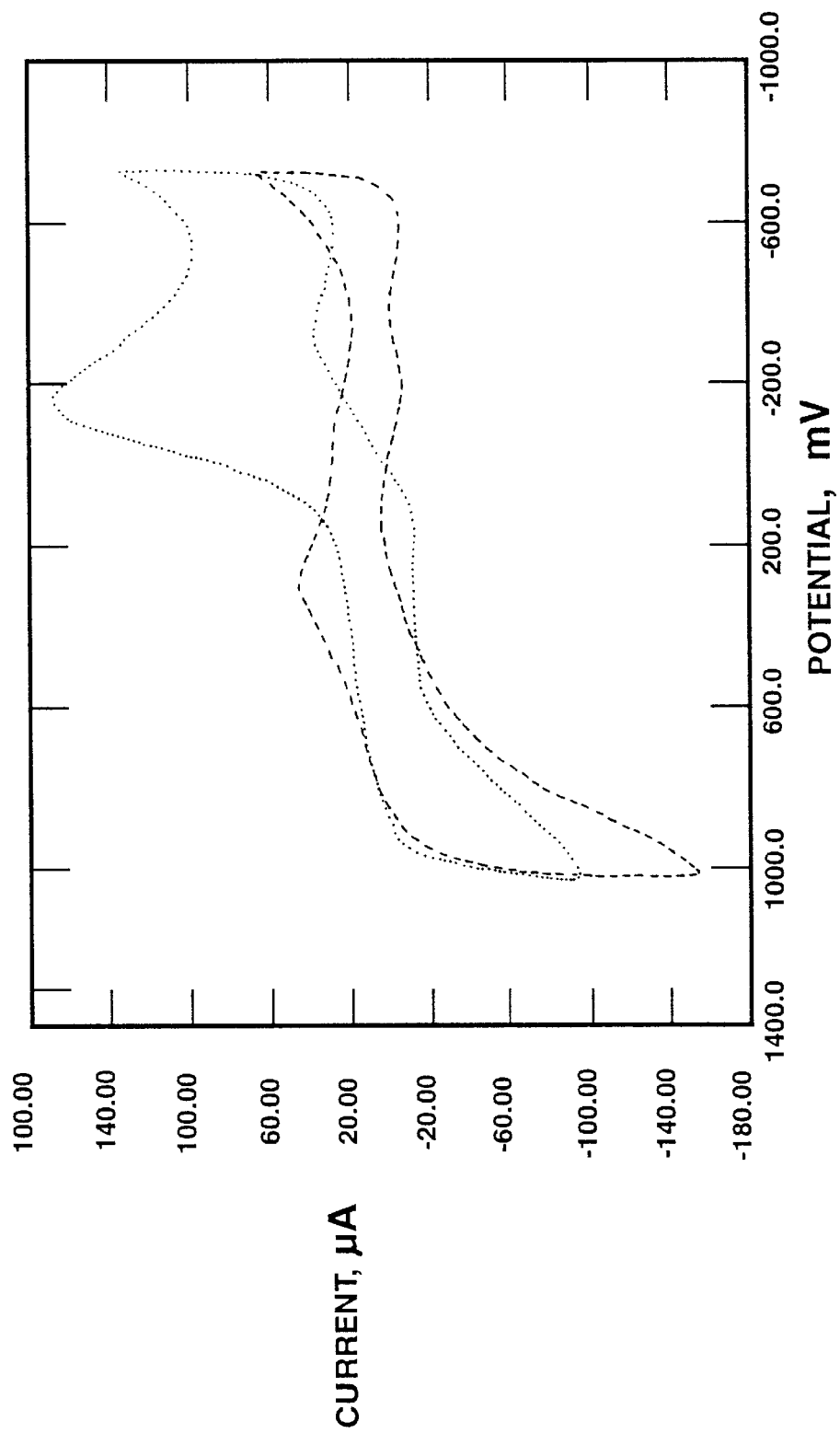
Figure 4:
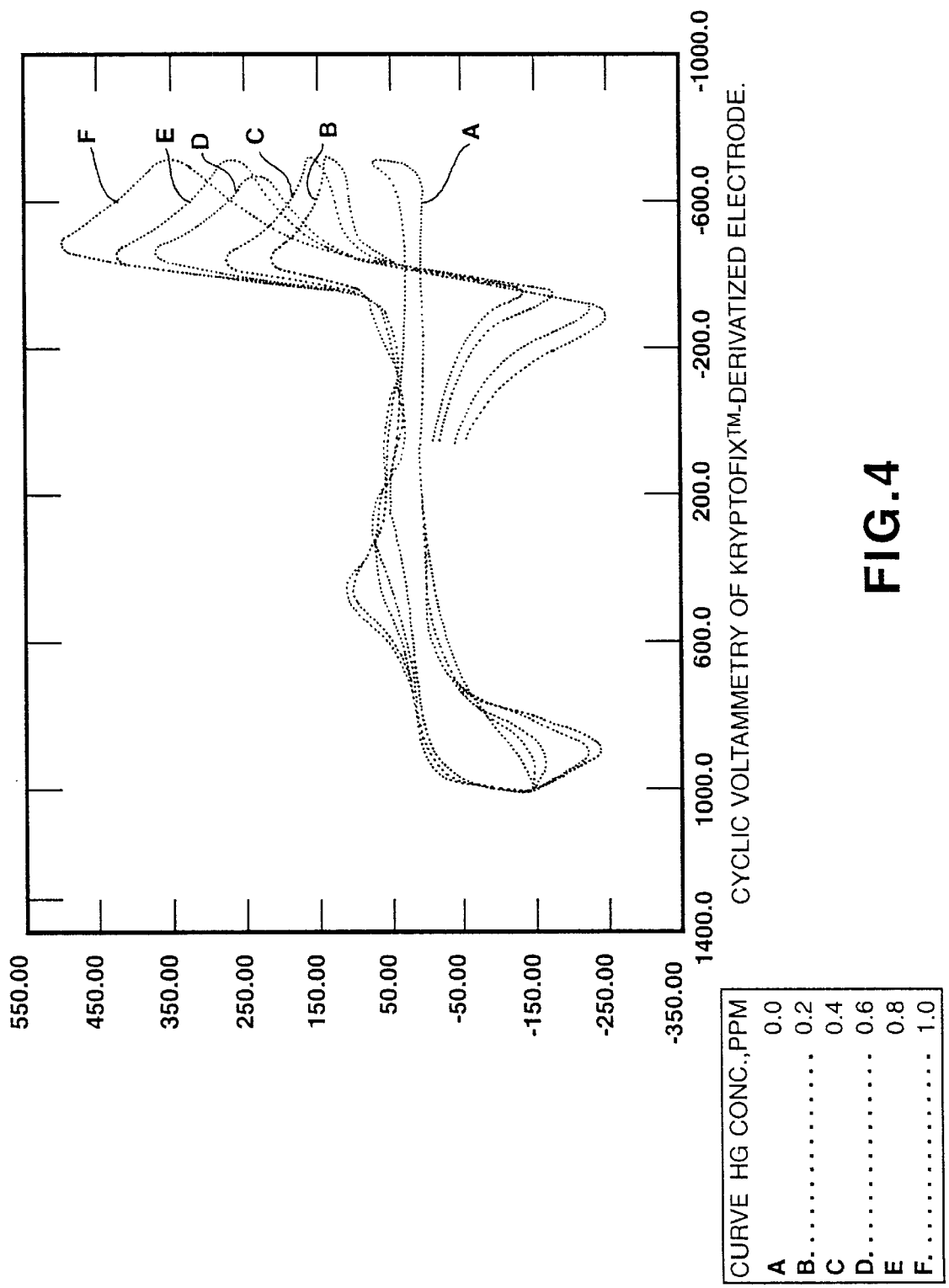

The following worked examples describe experimental preparations of the invented electrode material and data on testing thereof. Referring to FIGS. 1A–C, there is depicted the preparation of one, but not the only, embodiment of the electrode of the present invention, described below as comprising the steps of synthesis and electrodeposition. In FIG. 2, the equilibrium chemistry of the invented system is portrayed. In FIGS. 3–5, experimental data from the characterization and calibration of the invented probe is depicted.

Experimental: Worked Examples

Synthesis of the Derivatized Thiophene:

In this synthesis, 3-thiophene methanol (available from Aldrich Chemical) was converted to the chloride form by a SOCl$_2$ and pyridine halogen-substitution pathway, as indicated in FIG. 1A. The diaza crown ether was covalently attached by formation of a tertiary amine, as indicated in FIG. 1B. This derivatized thiophene structure was confirmed by Fourier transform infared (FTIR).

Electrodeposition of the Co-Polymer:

A 4:1 mole ratio of thiophene to the 3-Kryptofix-21™ derivatized thiophene was prepared in acetonitrile solution and deposited on the platinum substrate. The preferred potential for deposition was +0.7 V vs Ag/AgCl (sat'd KCl), as indicated by FIG. 1C. The electrodeposition time, an experimental variable that affects coating thickness, was about 1.5 minutes. Suggested times are preferably 0.1 to 2 minutes, but may be extended up to about 20 minutes for example. Deposition potential is an experimental variable, with preferred potentials being 0.7 to 1.0 V vs. Ag/AgCl.

Electrochemical Characterization:

The Kryptofix21™ derivatized electrodes constructed according to the above procedure were electrochemically characterized as follows, and compared to electrodes made with a copolymer not containing the chelating agent. Cyclic voltammetry was performed in a three-electrode cell. All data reported in FIG. 3 were obtained under the following conditions:

Electrolyte solution: aqueous 0.1 M NaClO$_4$

Counter electrode: bare Pt

Reference: aqueous Ag/AgCl (sat'd KCl)

Scan rate: 100 mv/s

Purge gas: N$_2$, electronic grade

Mercury concentration for the voltammetry characterization was changed by adding μL aliquots of a concentrated stock solution to the cell which had a volume of 35.0 ml. The stock solution was prepared from the pure metal dissolved in ultra-pure nitric acid and buffered to pH=5.5.

Discussion of Results of Worked Examples

The invented system is believed to work generally according to the schematic portrayal of equilibrium chemistry in FIG. 2. FIG. 2 shows that Hg$^{2+}$ is chelated to the agent with an equilibrium constant of $10^{16}$, which corresponds to an enhanced thermodynamic stability of the mercury-Kryptofix-21™ complex compared to that of other ions such as cadmium, lead and silver. The comparison of electrode surfaces by electrochemical characterization showed the results of such an equilibrium.

In FIG. 3, the selected Kryptofix-21™-derivatized electrode surface was compared to a polythiophene electrode surface without the chelating agent, by the electrochemical characterization technique described above in solutions containing no mercury. For the polythiophene probe coating, without chelate, the CV residual current curve has a large prominent cathodic wave at ~-0.18 V. The Kryptofix™-derivatized thiophene surface (also referred to as "Kryptofix™-derivatized electrode") has no wave in this region, and has a small peak at ~+0.3 V. Otherwise, the two electrodes have residual current curves with similar charging currents, and about the same discharge limits as depicted in FIG. 3.

Electrochemical characterization comparing the electrodes in solutions of various mercury concentrations was then performed and is shown in FIG. 4. In this testing, the Kryptofix-21™-derivatized electrode exhibited a reversible wave centered at ~-0.4 V vs SRE, which is attributed to the Hg$^+$/Hg$^{2+}$ couple. The invented electrode cathodically shifted the reduction potential of mercury due to the strength of the coordination bonds formed. The reversible wave for the derivatized thiophene is consistent with a one-electron process and shows the crown ether stabilizes both mercury (I) and mercury (II) ions. A cathodic wave at ~+0.5 V, associated with an anodic wave at ~+0.9 V, also responds to the level of mercury, and therefore was also attributed to oxidation of the ligand in the charge transfer complex.

Calibration of two Krytofix-21™-derivatized probes made according to the invention was performed, and the results are shown in FIG. 5. FIG. 5 shows the current response data at ~-0.45 V vs. SRE, for the two probes, normalized for geometric area. A linear response of current vs mercury concentration was seen. The cathodic peak current at ~-0.45 V exhibits this linear response to mercury (II) ions through several (~7) orders of magnitude, with a theoretical detection limit in the range of ~2 ppb, based on noise analysis of the data, and a criterion of signal/noise =3. This compares well with AA spectroscopy and other methods of mercury detection.

Thus, the invented copolymer and electrode were shown in these worked examples to be effective. The invented copolymer system for mercury detection and measurement is expected to have many advantages, summarized as follows:

a) preparation of the electrode is simple, reproducible and inexpensive, which compares very favorably with standard methods based on atomic absorption spectroscopy (AAS), including inductively coupled plasma (ICP) methods, which are very expensive and require trained operators;

b) the detection limit of this probe is less than about 2 ppb mercury, which compares very favorably with standard methods using AAS and ICP, which are expensive, operator-intensive methods with reproducible detection limits of about 0.5 ppb;

c) the working lifetime of this probe is about 1.5 years (possibly longer), compared to random polymer casts having lifetimes of from days to weeks;

d) the amperometric response is linear with mercury concentration over several orders of magnitude, which permits a wide dynamic operating range in solutions of widely ranging mercury concentrations;

e) dissolved O$_2$ has no observable effect on detection, which permits use of the probe in natural surface and ground waters, in situ;

f) technology is already in place to permit battery-powered operation;

g) sample collection of surface water is unnecessary, eliminating losses of volatile mercury analyte during sample storage, transport, handling and preparation;

h) the probe can be miniaturized for in vivo analysis in plants;

i) selectivity is very high over other metals likely to be present;

j) response time is in an acceptable range, about 1–3 minutes;

k) electrodes are readily prepared for reuse by discharging the mercury from the complex in an acid rinse; and l) Covalent attachment of the chelate into the polymer matrix prevents loss of the active binding site into the environment, and also ensures reproducible response over time.

Experimental variables in preparation and materials that impact on probe response include the following:

ratio of thiophene to derivatized thiophene in coating (suggested ratios are 1:1 up to 20:1);

film thickness, i.e. electrodeposition time (suggested times are 0.1 up to 20 minutes);

deposition potential (preferably 100 mV past E° for the polymerization); length of spacer arms on the thiophene (suggested lengths are 0 to 20 carbons with FIG. 1 showing one);

miniaturization by deposition onto conductive filament;

electrodeposition solvent and optional presence of electrolyte; and polymer rigidity, e.g., occurrence/amount of dithiophenylethane crosslinking.

Other monomers and other chelating or clathrating agents may be used in the subject invention. For example, aniline and pyrrole may be used as monomers. Alternative chelating/clathrating agents may be used to bind mercury to the probe, for example:

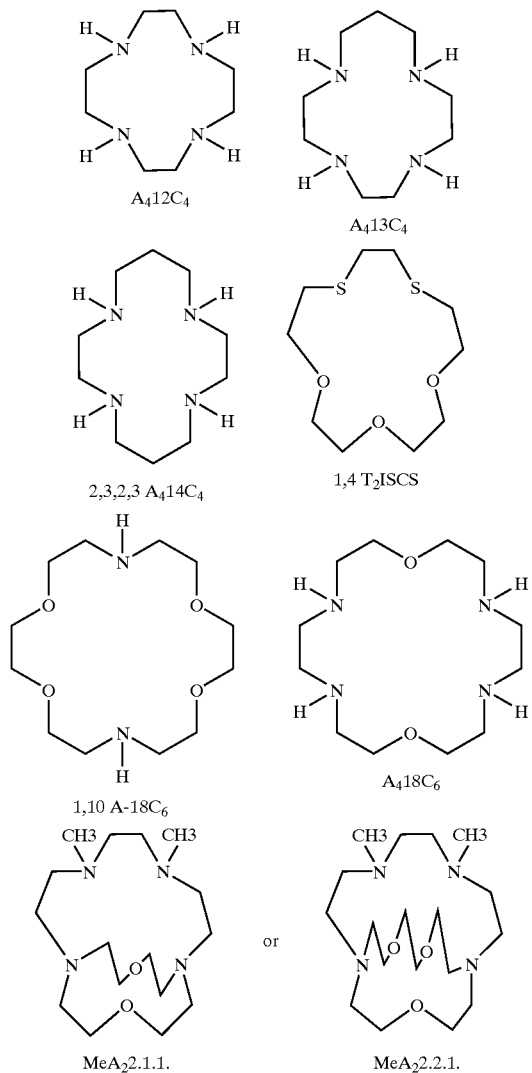

Alternative modes of operation are anticipated. For example, the invented device could be operated potentiometrically, in which case measured potential response would be linear with the logarithm of the mercury concentration. Also, the invented device could be operated in a way such that capacitance is the response variable being measured.

Although this invention has been described above with reference to particular means, materials and embodiments, it is to be understood that the invention is not limited to these disclosed particulars, but extends instead to all equivalents within the scope of the following claims.

I claim:

1. An electrode surface for detecting mercury, the electrode surface comprising a monomer of thiophene, aniline or pyrrole having a crown ether-derived functional group.

2. An electrode surface as in claim 1, wherein the functional group is derived from 1,4,10-trioxa-7,13-diazacyclopentadecane.

3. An electrode surface as in claim 1, wherein the monomer is thiophene derivatized by covalent attachment of said functional group.

4. An electrode surface as in claim 1, further comprising thiophene copolymerized with the monomer having the crown ether-derived functional group.

5. An electrode surface for detecting mercury, the electrode surface comprising a copolymer of a monomer of thiophene, aniline or pyrrole having a covalently-bonded chelating agent.

6. An electrode surface as in claim 5, wherein the chelating agent is derived from 1,4,10-trioxa-7,13-diazacyclopentadecane.

7. An electrode surface for detecting mercury, the electrode surface comprising a copolymer of a monomer of thiophene, aniline or pyrrole having a covalently-bonded clathrating agent.

8. An electrode surface for detecting mercury, the electrode surface comprising a monomer of thiopyene, aniline or pyrrole having a functional group derived from a compound from the group consisting of:

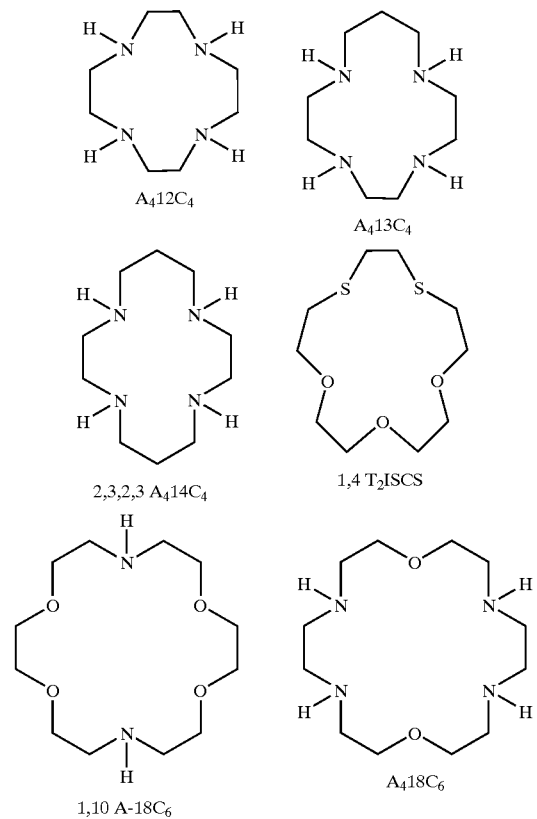

-continued

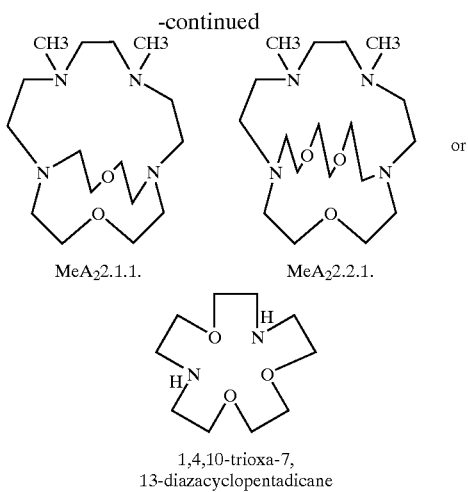

MeA₂2.1.1.   MeA₂2.2.1.

1,4,10-trioxa-7,
13-diazacyclopentadicane

9. A copolymer comprising a thiophene monomer and a thiophene monomer having a functional group derived from a compound from the group consisting of:

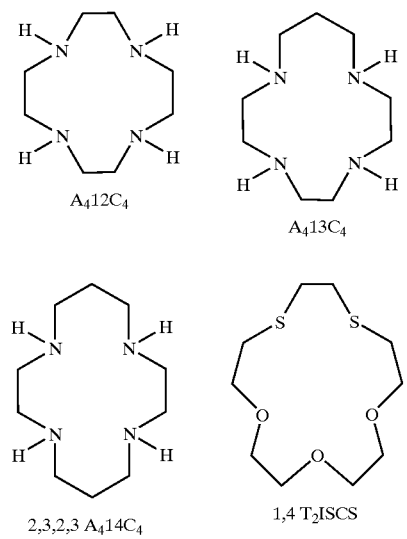

A₄12C₄   A₄13C₄

2,3,2,3 A₄14C₄   1,4 T₂ISCS

-continued

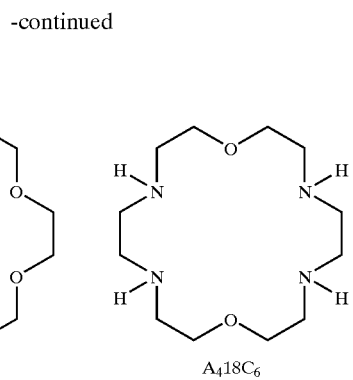

1,10 A-18C₆   A₄18C₆

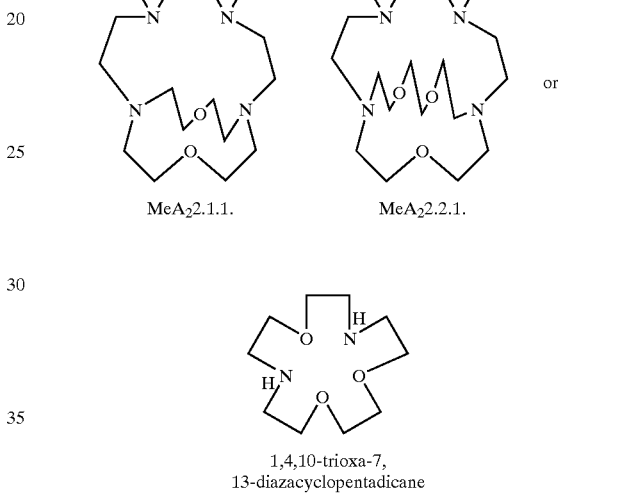

MeA₂2.1.1.   MeA₂2.2.1.

1,4,10-trioxa-7,
13-diazacyclopentadicane

10. A copolymer as in claim 9, wherein the functional group is derived from 1,4,10-trioxa-7,13-diazacyclopentadecane.

* * * * *